United States Patent
Zhang et al.

(10) Patent No.: US 11,944,784 B2
(45) Date of Patent: Apr. 2, 2024

(54) COMBINED ANALYTE SENSOR AND INFUSION SET

(71) Applicant: MEDTRONIC MINIMED, INC., Northridge, CA (US)

(72) Inventors: Guangping Zhang, Calabasas, CA (US); Kiem H. Dang, Northridge, CA (US); Valerie Chen, Santa Clarita, CA (US); Ling Jiang, Northridge, CA (US); Evan Anselmo, Northridge, CA (US); Zhiwu Fang, Newbury Park, CA (US); Sarnath Chattaraj, Simi Valley, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 547 days.

(21) Appl. No.: 16/687,481

(22) Filed: Nov. 18, 2019

(65) Prior Publication Data
US 2021/0146047 A1 May 20, 2021

(51) Int. Cl.
*A61M 5/172* (2006.01)
*A61B 5/145* (2006.01)
*A61M 5/14* (2006.01)
*A61M 5/142* (2006.01)
*A61M 5/168* (2006.01)

(52) U.S. Cl.
CPC ....... *A61M 5/1723* (2013.01); *A61B 5/14532* (2013.01); *A61M 5/1413* (2013.01); *A61M 5/14248* (2013.01); *A61M 5/16836* (2013.01)

(58) Field of Classification Search
CPC .............. A61M 5/1723; A61M 5/1413; A61M 5/14248; A61M 5/16836; A61B 5/14532
See application file for complete search history.

(56) References Cited

U.S. PATENT DOCUMENTS

| | | | |
|---|---|---|---|
| 1,065,483 A | * | 6/1913 | Turner ............... F16C 11/0619 439/8 |
| 4,755,173 A | | 7/1988 | Konopka et al. |
| 5,391,250 A | | 2/1995 | Cheney, II et al. |
| 5,485,408 A | | 1/1996 | Blomquist |
| 5,522,803 A | | 6/1996 | Teissen-Simony |
| | | (Continued) | |

FOREIGN PATENT DOCUMENTS

| | | |
|---|---|---|
| EP | 2457606 A1 | 5/2012 |
| WO | 2017184801 A1 | 10/2017 |

OTHER PUBLICATIONS

"USB Hardware." Wikipedia, Wikimedia Foundation, May 2, 2023, en.wikipedia.org/wiki/USB_hardware. Accessed May 20, 2023. (Year: 2019).*

(Continued)

*Primary Examiner* — David J. McCrosky
*Assistant Examiner* — Clarissa Cuevas
(74) *Attorney, Agent, or Firm* — Foley & Lardner LLP

(57) ABSTRACT

Disclosed herein are combined devices and methods of manufacturing such combined devices. The combined devices disclosed herein include an analyte sensor including a sensor probe; an infusion set hub including a cannula; and a flexible base. The analyte sensor and infusion set hub are attached to the flexible base such that movement of one of the analyte sensor and the infusion set hub is substantially not transferred to the other one of the analyte sensor and the infusion set hub.

21 Claims, 12 Drawing Sheets

(56) References Cited

U.S. PATENT DOCUMENTS

| | | |
|---|---|---|
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0123819 A1 | 5/2007 | Mernoe et al. |
| 2008/0319414 A1 | 12/2008 | Yodfat et al. |
| 2009/0062767 A1* | 3/2009 | Van Antwerp ....... A61B 5/6849 600/316 |
| 2010/0160861 A1 | 6/2010 | Causey, III et al. |
| 2017/0184801 A1 | 6/2017 | Isenhour et al. |
| 2018/0280608 A1* | 10/2018 | Gillett ................. A61M 5/3287 |
| 2021/0386930 A1* | 12/2021 | Lanigan ................ A61M 5/158 |
| 2021/0402084 A1* | 12/2021 | Coker ............... A61M 25/0606 |

OTHER PUBLICATIONS

"90 Pcs XHF Conductor Compact Connectors Lever Connectors Nuts, Electrical Connectors Wire Terminals for Any Circuit Inline Splices 28-12 AWG" Amazon, www.amazon.com/dp/B07FT1G8YN/ref=sspa_dk_detail_4?pd_rd_i=B07FT1G8YNpd_rd_w=FQTJncontent-id=amzn1.sym.eb7c1ac5-7c51-4df5-ba34-ca810f1 (Year: 2019).*

* cited by examiner

400

COMBINED ANALYTE SENSOR AND INFUSION SET

TECHNICAL FIELD

Embodiments of the subject matter described herein relate generally to combined devices including both an analyte sensor and an infusion set hub.

BACKGROUND

Glucose is one of the main sources of energy for the cells that make up muscle and other tissue. Glucose is absorbed into the bloodstream, where it enters cells with the help of insulin. Some individuals with diabetes suffer a chronic condition in which the pancreas produces little or no insulin, thereby reducing the uptake of glucose by cells. Blood glucose levels will therefore remain high unless a person takes steps to manage their high blood sugar. The effects of diabetes can become medically serious if not correctly managed.

One way of managing this lack of insulin is through the use of an insulin pump. Insulin pumps are devices that allow for the delivery of insulin to a user. This insulin is typically delivered subcutaneously under the user's skin.

The amount of insulin and the timing of the insulin delivery is normally determined based on the user's glucose levels. For example, if the user has a high level of blood glucose concentration at a particular time, this level being outside of a pre-determined threshold level for that user, insulin may be delivered to the user via an insulin infusion set worn on the user's body.

A user's glucose concentration levels may be monitored using a continuous analyte sensor, such as a continuous glucose sensor, which may be worn on the user's body. Continuous glucose sensors are able to monitor glucose levels in the interstitial fluid (ISF) of a user over an extended period of time, with blood-glucose concentration readings typically being taken periodically via finger pricking. There is a 5 to 10-minute delay in ISF glucose response to changes in blood glucose. Glucose readings on ISF have been proven to reliably reflect glucose levels.

It is desirable to improve user comfort when wearing glucose sensors and infusion sets on the body.

Furthermore, other desirable features and characteristics will become apparent from the subsequent detailed description and the appended claims, taken in conjunction with the accompanying drawings and the foregoing technical field and background.

BRIEF SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. Although the majority of the inventive concepts discussed herein will be described with respect to a glucose sensor and an insulin infusion set hub, it will be appreciated that these concepts are also applicable to other types of analyte sensors and infusion set hubs.

According to an exemplary embodiment, there is provided a combined device. The combined device includes an analyte sensor. In various embodiments, the analyte sensor is a single-use, disposable sensing component designed to be used with a portable potentiostat device that may record and/or transmit data to a monitor (e.g. a glucose sensor may transmit data to an insulin pump), or alternatively with a recording device for use with retrospective sensor evaluation. The combined device includes an infusion set hub. The infusion set hub includes a cannula through which a fluid to be infused (such as insulin) may be delivered from a medication reservoir via a pump. The combined device also includes a flexible base. The analyte sensor and infusion set hub are attached to the flexible base such that a movement of one component (i.e., movement of the analyte sensor or movement of the infusion set hub) does not cause a substantial movement of the other component (i.e., the other one of the infusion set hub or the analyte sensor).

According to a second exemplary embodiment, there is provided a method of manufacturing a combined device. The method includes the step of providing a flexible base; attaching an infusion set hub to the flexible base; and attaching an analyte sensor to the flexible base.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Combining a continuous analyte sensor, such as a glucose sensor, and an infusion set, such as an insulin infusion set, together into one device reduces the number of locations on the user's body that have to be "managed" by the user during bathing, exercise and so on. As such, a combined device requires less management by a user, and therefore improves user experiences with wearing the analyte sensor and the infusion set hub.

After an extensive study, the present inventors recognized some disadvantages associated with combined analyte sensor/infusion set hub devices. One of these disadvantages will be explained with reference to FIG. 1.

Figure 1:
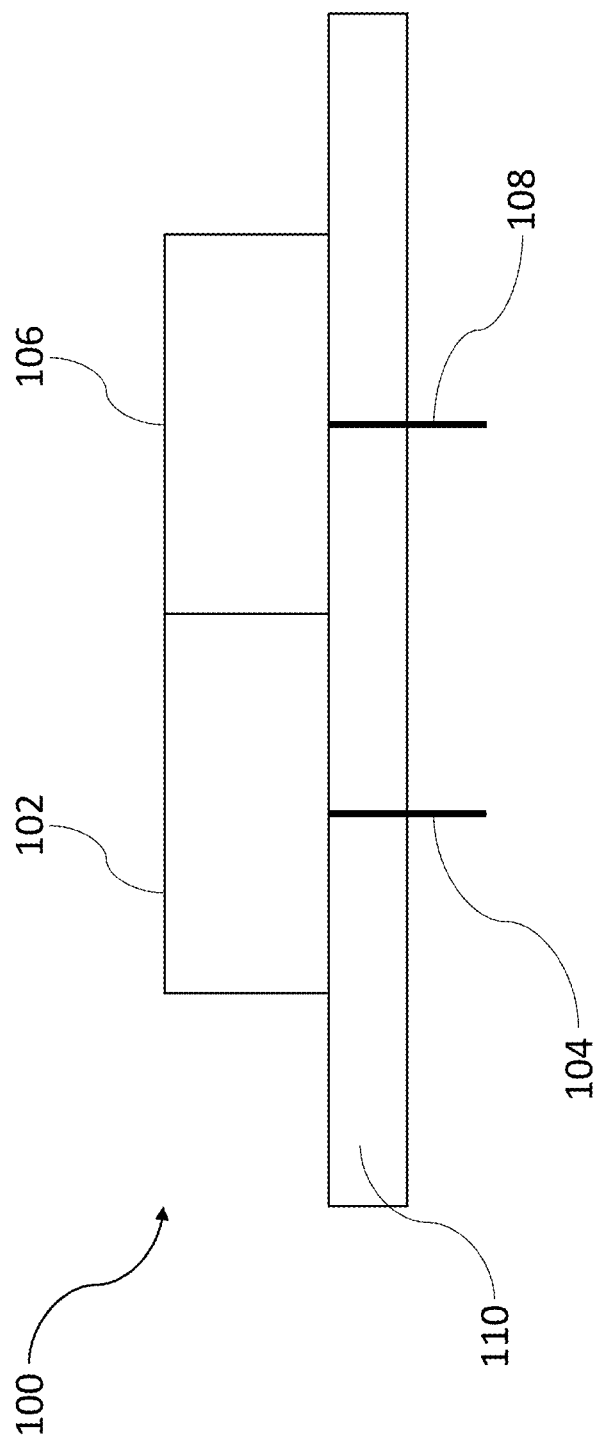
FIG. 1 is a schematic view of a combined analyte sensor and infusion set hub device.

FIG. 1 shows a schematic of a combined analyte sensor/infusion set device 100 (hereinafter referred to as a "combined device"). The combined device 100 comprises a glucose sensor 102 and an insulin infusion set hub 106 fixedly attached to one another. The glucose sensor 102 comprises a sensor probe 104. The sensor probe 104 is an intradermal probe that, when installed, is configured to be partially disposed beneath the user's skin to allow for electrochemical sensing of the user's glucose concentration in the interstitial fluid. The insulin infusion set hub 106 includes a cannula 108 configured to provide a channel from an insulin reservoir to the user's tissue, such that insulin may be delivered through the cannula 108.

Both of the glucose sensor 102 and the insulin infusion set hub 106 are attached to a solid base 110, with the sensor probe 104 and cannula 108 protruding through the solid base 110. In use, the solid base 110 may be affixed to the user's skin via an adhesive, via bandages, and so on, with the sensor probe 104 and cannula 108 being located intradermally on user's skin. The user's glucose concentration is monitored by the glucose sensor 102 of the combined device 100 and, when necessary, the insulin infusion set hub 106 of the combined device 100 is used to deliver insulin to the user in order to regulate the user's glucose concentration to a desired level.

One problem with this type of combined device 100 is that the solid base 110 and the fixed attachment between the glucose sensor 102 and insulin infusion set hub 106 each contributes to a "see-saw" effect during or after the intradermal installation of the sensor probe 104 and cannula 108 on the user. More specifically, a vertical or horizontal movement of the insulin infusion set hub 106 (whether this movement is deliberate or accidental) causes a resultant, corresponding displacement of the glucose sensor 102 about a point near the center of the combined device 100, and vice versa, which can be problematic. In use, the sensor probe 104 (and to a lesser extent the cannula 108) should ideally sit in substantially the same position in the user's tissue from installation and throughout subsequent use. This constant position allows, for example, for the sensor probe to be calibrated accurately during a "calibration phase" of the glucose sensor 102 for that particular location. However, due to the fixed attachment between the glucose sensor 102 and the insulin infusion set hub 106 and/or the attachment of each of the glucose sensor 102 and the insulin infusion set hub 106 to the solid base 110, the above-described "see-saw" effect promotes undesirable movement of the sensor probe 104 and/or the cannula 108 to a new, uncalibrated position.

In order to overcome this problem, exemplary embodiments provide a combined device where this "see-saw" effect is reduced.

Figure 2:
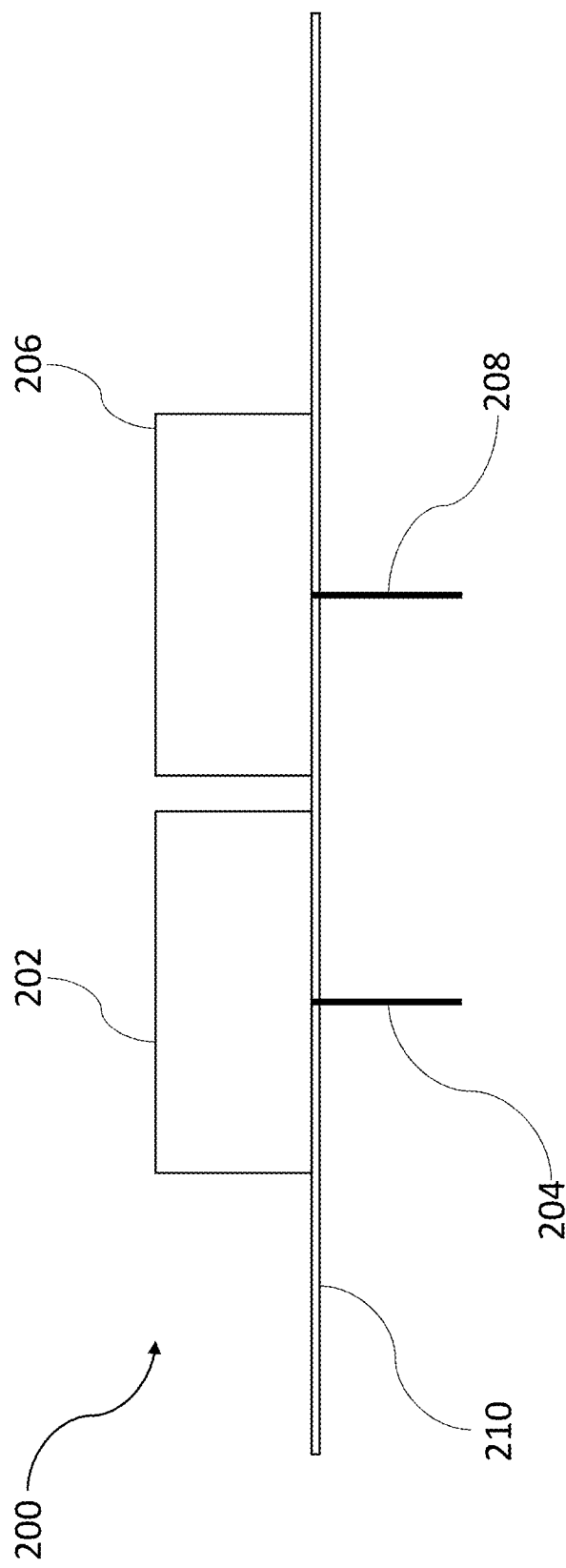
FIG. 2 is a schematic view of a combined analyte sensor and infusion set hub device according to exemplary embodiments.

A schematic of a combined device 200 according to an exemplary embodiment is shown in FIG. 2. As can be seen in FIG. 2, the combined device 200 includes a glucose sensor 202 including a sensor probe 204 and an insulin infusion set hub 206 including a cannula 208. The glucose sensor 202 and the insulin infusion set hub 206 are arranged proximate to each other on a flexible base 210. In an embodiment, the glucose sensor 202 and the insulin infusion set hub 206 are not attached to one another and are only attached to the flexible base 210, such that movement of one of these devices does not result in a substantial movement of the other device. In particular, because the base 210 is flexible, no "see-saw" effect is caused by the movement of one of the devices attached to the flexible base. In an alternative exemplary embodiment, the glucose sensor 202 and the insulin infusion set hub 206 are connected to one other via a joint that allows for horizontal and vertical displacements of either one of these devices without inducing an opposite displacement in the other device, as will be described in more detail below.

Due to the substantial mechanical isolation between the glucose sensor 202 and the insulin infusion set hub 206 caused by attaching the glucose sensor 202 and the insulin infusion set hub 206 only to a flexible base 210 and not to each other in a fixed manner, or by attaching the glucose sensor 202 and the insulin infusion set hub 206 to each other in a manner that allows for horizontal and vertical displacements of either one of these devices without inducing a substantial opposite displacement in the other device (for example by a joint), any accidental or deliberate movements of one device will have substantially no effect on the position of the other device. As such, the likelihood of undesired movement of either the sensor probe 204 or the cannula 208 is reduced. Due to this reduced likelihood of undesired movement of the sensor probe, a high level of accuracy of the sensor probe 204 may be maintained over its entire operational lifespan. In particular, since the calibration process for the sensor probe 204 occurs when the installed sensor probe 204 is in a particular position, movement of the sensor probe 204 from that position could decrease the accuracy of readings of the glucose sensor 202, and retention of the sensor probe 204 in the same position maintains a high level of accuracy.

Figure 3:
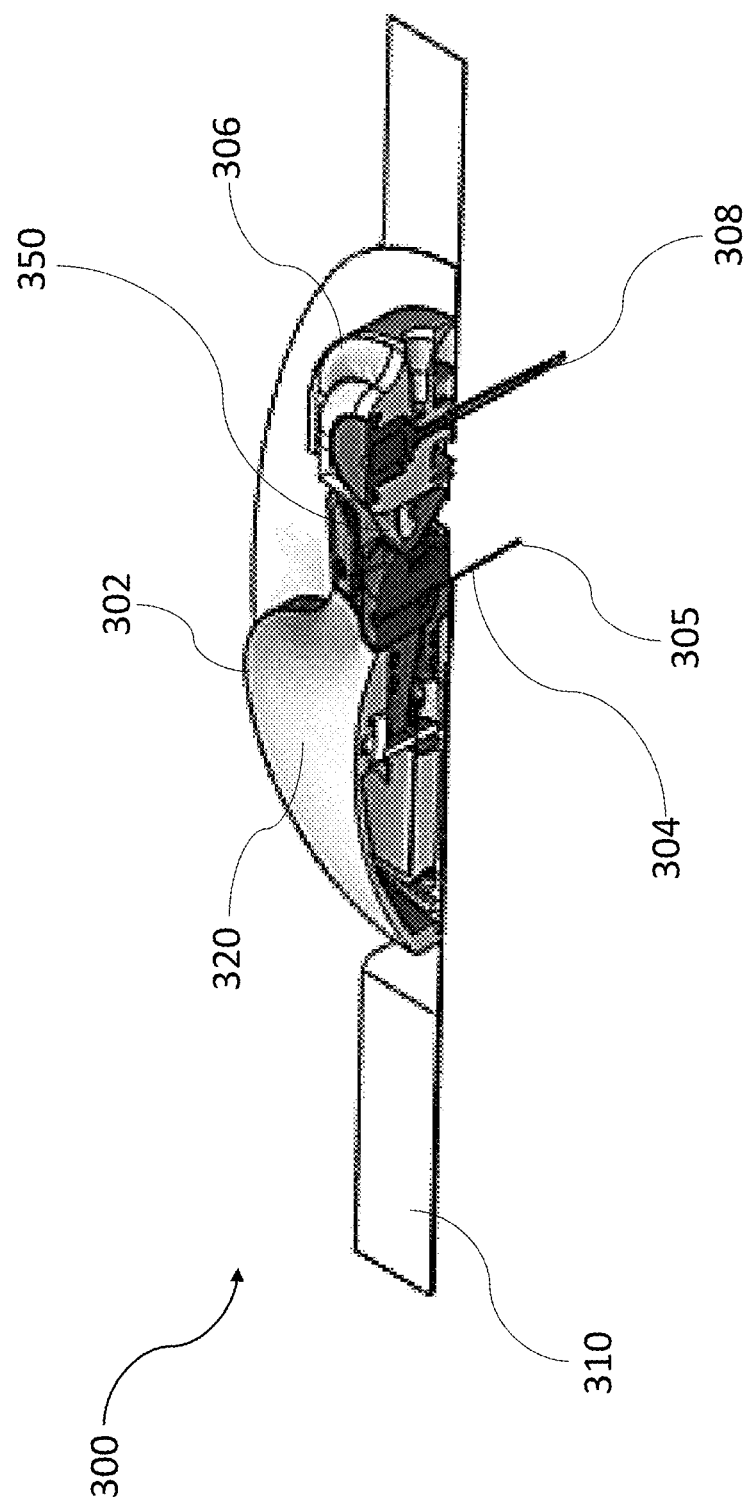
FIG. 3 is an isometric side view of a combined device according to exemplary embodiments.

An isometric view of a combined device 300 according to exemplary embodiments is shown in FIG. 3. As can be seen in FIG. 3, the combined device includes a glucose sensor 302 attached to a flexible base 310, wherein the glucose sensor 302 includes a sensor probe 304. In various exemplary embodiments, the glucose sensor 302 is attached to the flexible base 310 by welding. In alternative exemplary embodiments, the glucose sensor 302 is attached to the flexible base 310 by another means of attachment, such as via an adhesive, by stitching, by stitch welding, and so on.

In exemplary embodiments, the glucose sensor 302 comprises a transmitter 320 configured to transmit a sensed glucose concentration value from the glucose sensor 302 to the insulin infusion set hub 306. In an exemplary embodiment, the transmitter 320 is configured to wirelessly transmit the sensed glucose concentration value to the pump which controls insulin flowing through the infusion set hub 306. In an alternative exemplary embodiment, the transmitter 320 is configured to transmit the sensed glucose concentration value via a wired connection through the insulin infusion set hub to the pump.

As shown in FIG. 3, in exemplary embodiments the sensor probe 304 is angled with respect to the flexible base. The angle of the sensor probe 304 is selected such that a tip 305 of the sensor probe 304, when installed in a user, will be disposed in interstitial tissue of the user. This allows for electrochemical measurement to be taken of the user's interstitial fluid glucose concentration, which is indicative of the user's blood-glucose concentration.

The combined device 300 further includes an insulin infusion set hub 306 attached to the flexible base 310, wherein the insulin infusion set hub 306 includes a cannula 308. In various exemplary embodiments, the insulin infusion set hub 306 is attached to the flexible base 310 by welding. In alternative exemplary embodiments, the insulin infusion set hub 306 is attached to the flexible base 310 by another means of attachment, such as via an adhesive, by stitching, by stitch-welding, and so on.

The glucose sensor 302 and the insulin infusion set hub 306 in FIG. 3 are connected to each other via a joint 350. The joint 350 is configured to allow for three-dimensional movement of either one of the glucose sensor 302 or the insulin infusion set hub 306 without transferring this movement to the other one of the glucose sensor 302 or the insulin infusion set hub 306. In other words, the joint 350 is configured to substantially isolate the glucose sensor 302 from movement of the insulin infusion set hub 306 and vice versa.

In an exemplary embodiment, the joint 350 comprises complementary angled sections of the housing of the glucose sensor 302 and the insulin infusion set hub 306 such that movement of either one of the glucose sensor 302 and the insulin infusion set hub 306 is not transferred to the other one of the glucose sensor and the insulin infusion set hub 306. In an alternative exemplary embodiment, the joint 350 comprises a ball-and-socket joint.

In a preferred embodiment, the joint 350 is configured to allow for a releasable attachment to be formed between the glucose sensor 302 and the insulin infusion set hub 306. In this manner, the combined device 300 can be made modular in nature, such that either one of the glucose sensor 302 or the insulin infusion set hub 306 can be replaced without having to replace the entire combined device 300. It will be appreciated that a modular configuration can also be achieved when the glucose sensor 302 is not connected to the insulin infusion set hub.

By making the combined device 300 modular in nature, the ease of use and the user-comfort of the combined device 300 is improved. In particular, if either one of the glucose sensor 302 or the insulin infusion set hub 306 is non-functional upon installation, or fails during subsequent use, this specific component of the combined device 300 may be replaced without having to replace the other component of the combined device. This reduces the overall number of sensor probe 304 and cannula 308 installations required.

A number of techniques are envisaged to make the combined device 300 modular in nature. In a first exemplary embodiment, each of the glucose sensor 302 and the insulin infusion set hub 306 are directly attached to the flexible base 310 directly with an adhesive and are mechanically isolated from one another. In this manner, a user can simply apply a force to either one of the glucose sensor 302 or insulin infusion set hub 306 so as to mechanically detach either component from the flexible base 310. A replacement glucose sensor 302 or insulin infusion set hub 306 can then be installed by attaching this replacement component to the flexible base 310 with adhesive.

In another exemplary embodiment, each of the glucose sensor 302 and the insulin infusion set hub 306 are directly attached to the flexible base 310 directly with an adhesive and are releasably connected via the joint 350. In order to replace either one of the glucose sensor 302 or the insulin infusion set hub 306, the user can apply a force to the component to be replaced to thereby mechanically detach the component from the base 310 and concurrently release the component from the joint 350. A replacement glucose sensor 302 or insulin infusion set hub 306 can then be installed by attaching this replacement component to the flexible base 310 with adhesive and concurrently forming the joint 350.

Figure 4:
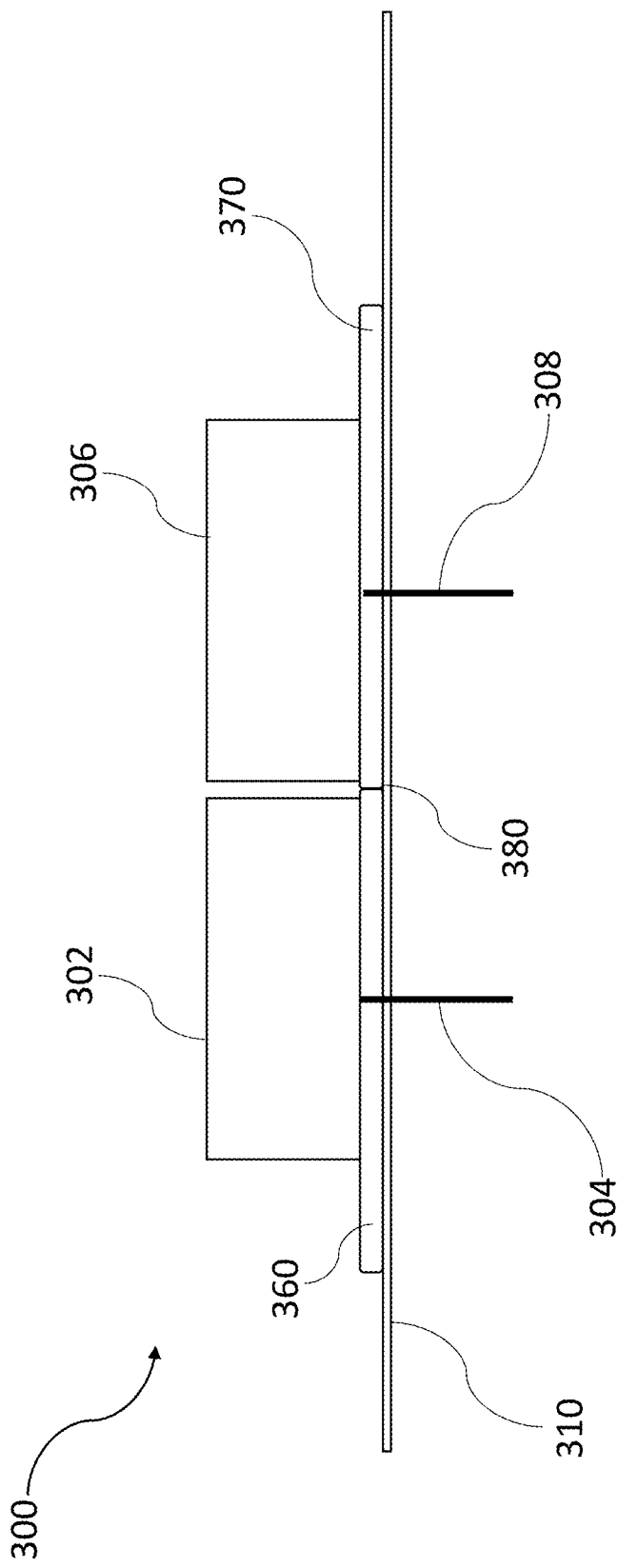
FIG. 4 is a schematic view of another combined device according to exemplary embodiments.

In an exemplary embodiment, schematically shown in FIG. 4, each one of the glucose sensor 302 and the insulin infusion set hub 306 are permanently attached to respective first and second connectors 360, 370, for example by stitching or welding. The first and second connectors 360, 370 are releasably attached to the flexible base 310, for example by an adhesive. In exemplary embodiments, the first and second connector 360, 370 are connected to the flexible base 310 via an adhesive. In this manner, the user can apply a force to one of the first and second connectors 360, 370 in order to detach this connector and the component (the glucose sensor 302 or the insulin infusion set hub 306) attached to the connector from the flexible base 310. To assist the user in detaching the connectors 360, 370 from the flexible base 310, in exemplary embodiments the connectors 360, 370 are shaped so as to have a tab portion that the user is able to grasp and pull when detaching the connector from the flexible base 310. In an exemplary embodiment, the first and second connectors 360, 370 are formed from a unitary piece of material, with perforations 380 formed between the first and second connectors 360, 370 so as to allow for the first and second connectors 360, 370 to be pulled apart by the user when replacing one of the glucose sensor 302 and the insulin infusion set hub 306.

It has been determined by the present inventors that by allowing for modular replacement of the glucose sensor 302 and the insulin infusion set hub 306, the overall lifetime and reliability of the combined device 300 can be increased.

Returning to FIG. 3, it can be seen that the sensor probe 304 is located in close proximity to the cannula 308 of the insulin infusion set hub 308. It will be appreciated that locating the sensor probe 304 relatively close to the cannula 308 is a necessity for forming a combined device 300 where the glucose sensor 302 and the insulin infusion set hub 306 are located at the same site on the user's body.

The present inventors recognized a potential issue with locating the sensor probe 304 of the glucose sensor 302 relatively close to the cannula 308. In particular, as insulin is delivered into the user's tissue by the cannula 308, the local insulin concentration is increased. As there are other components (e.g. preservatives and surfactants) in insulin formulation which impact the glucose sensor's chemical performance, this local insulin concentration increase causes the likelihood of incorrect sensor readings to increase. If the sensor probe 304 is also disposed in this local area, the glucose sensor 302 will therefore be more likely to disadvantageously detect an incorrect glucose concentration to arrive at an incorrect overall glucose concentration reading for the user (which phenomenon is hereinafter referred to as "cross-talk").

To study how to mitigate against the effects of such cross-talk, the present inventors investigated the minimum distance between the sensor probe 304 and the cannula 308. From the results of this study, it was determined that a distance of at least 5 mm was required by the sensor probe 304 and the cannula 308 in order to sufficiently reduce the effects of cross-talk, for example a distance of between about 5 mm and about 20 mm. Preferably, a distance of at least 10 mm is present between the cannula 308 and the sensor probe 304 to reduce the effects of cross-talk, such as between about 10 mm and about 15 mm. For example, a distance of about 13 mm between the cannula 308 and the sensor probe 304 allows for a reduction in the effects of cross-talk whilst also ensuring the overall combined device is kept sufficiently compact for user comfort.

Figure 5:
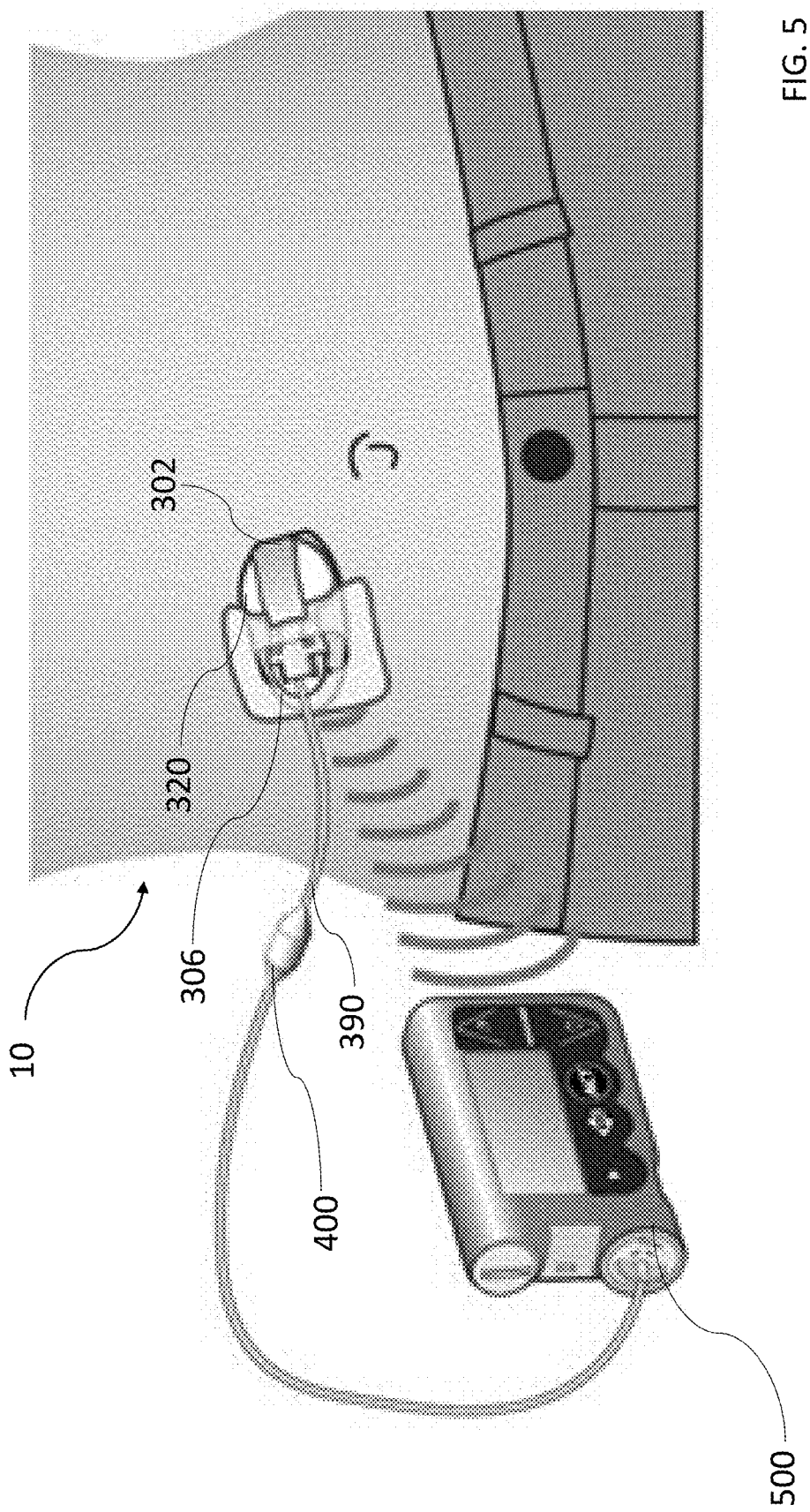
FIG. 5 is an isometric view of a combined device according to exemplary embodiments disposed on a user's body.

Turning now to FIG. 5, another isometric view of the combined device 300 is shown, with the combined device 300 being installed on a site on the user's body 10. As described above, the combined device 300 includes a glucose sensor 302 with a transmitter 320. In the embodiment shown in FIG. 5, the transmitter 320 is a wireless transmitter configured to wirelessly transmit a sensed ISF glucose concentration level. The combined device 300 further includes an insulin infusion set hub 306. The insulin infusion set hub 306 is connected via an insulin delivery tube 390 to a connector 400. The connector 400 is configured to releasably connect the insulin delivery tube 390 to an insulin pump and reservoir 500.

In use, the glucose sensor 302 senses the user's glucose concentration and wirelessly transmits this value to a user device (such as the pump 500) for displaying to the user. When the user's glucose concentration satisfies a certain criterion (such as exceeding a predetermined threshold), the pump 500 is then operated (either by the user or automatically) so as to administer insulin to the user via the insulin delivery tube 390 and cannula.

Figure 6:
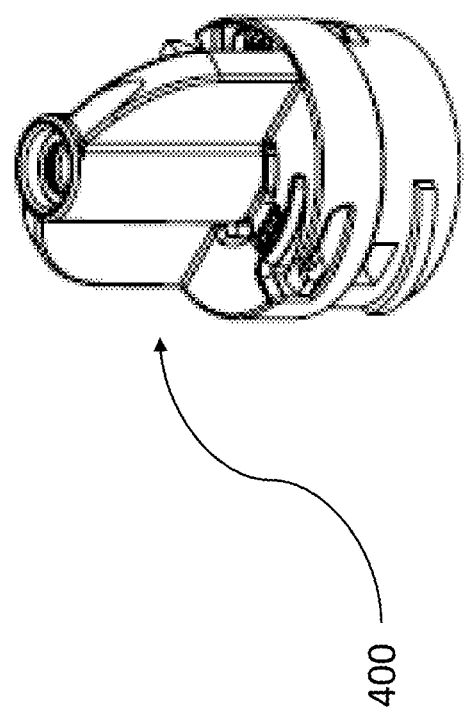
FIG. 6 is an isometric view of a connector to be used with the combined device according to exemplary embodiments.

A "quick-fit" connector is used to connect the insulin delivery tube 390 to a medication reservoir, which is typically located inside the pump 500. In an exemplary embodiment, the connector 400 comprises a one-piece H-cap connector. Such a connector is shown in FIG. 6. A H-cap connector 400 allows for quick connection and disconnection of the pump 500 to the insulin delivery tube 390, and also reduces the potential for leakage from this connection. In addition, the H-cap connector 400 comprises an in-line filter and 2 PVA foams, which along with the low-preservative-loss tubing, allows for clean insulin to pass through the infusion set fluid path and to be infused through the cannula for a period of up to seven days.

Figure 7:
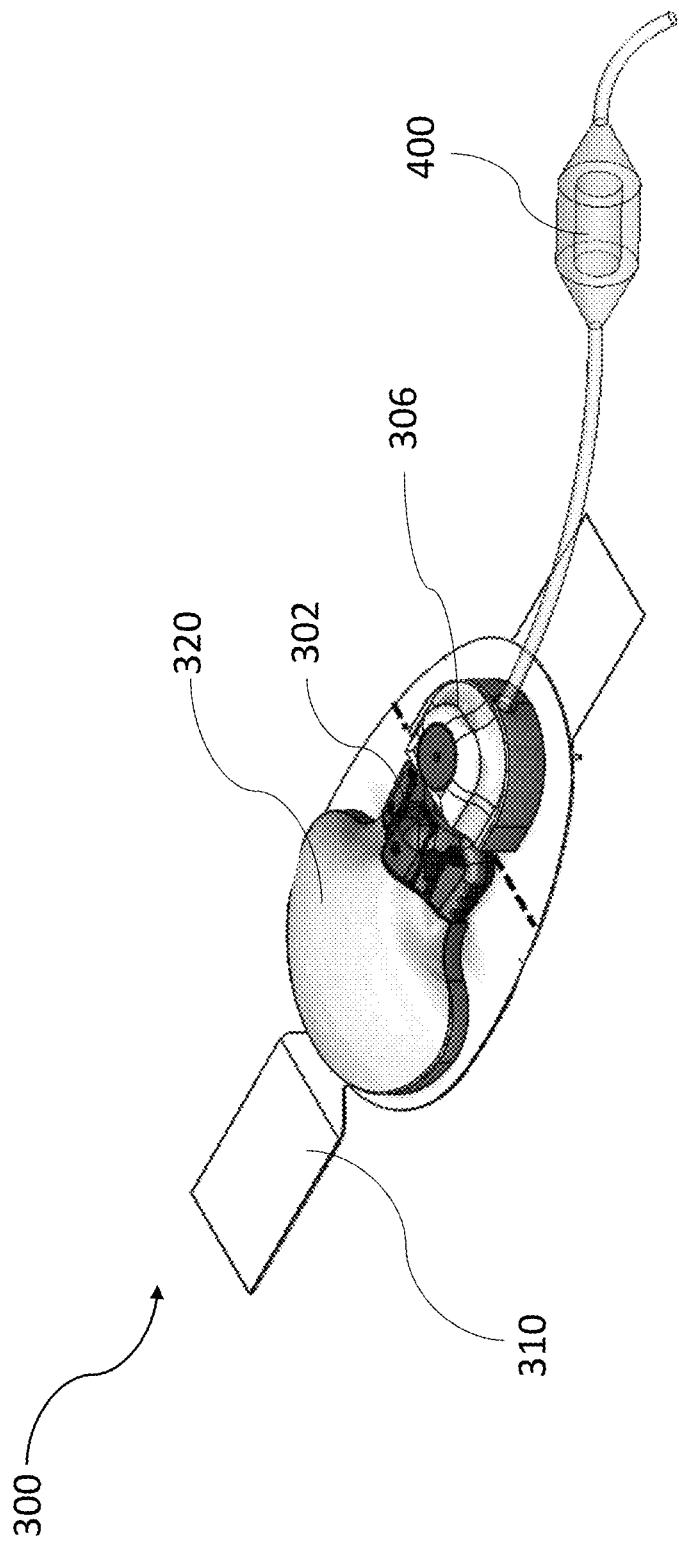
FIG. 7 is another isometric view of a combined device according to exemplary embodiments.
Figure 8:
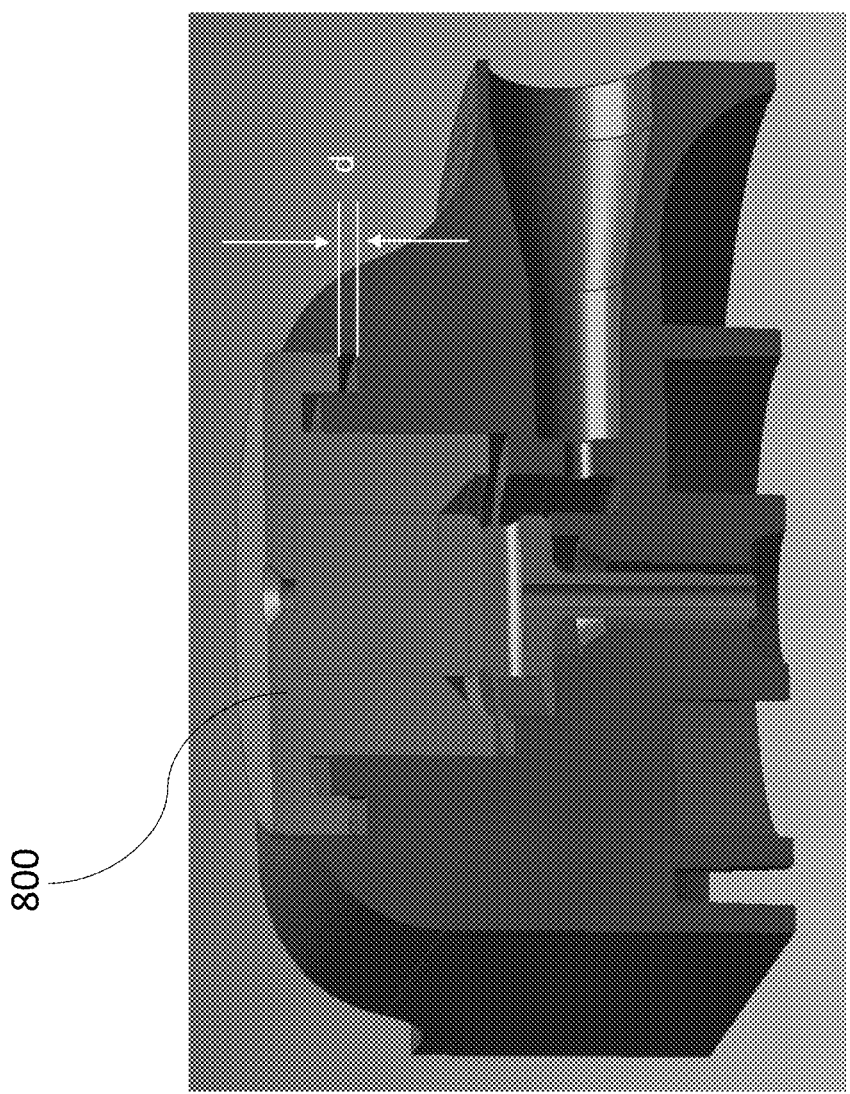
FIG. 8 shows an infusion set hub according to exemplary embodiments which was used in a stress/strain simulation.

Turning now to FIG. 7, an isometric view of an exemplary embodiment of the combined device 300 is shown. As can be seen in the exemplary embodiment FIG. 7, the vertical profile of the insulin infusion set hub 306 is reduced so as to reduce the likelihood that the combined device 300 will "catch" on the user's clothing. Preferably, the maximum vertical dimension of the combined device, which is herein defined as the distance between the bottom of the flexible base to the end of the combined device furthest away, in a perpendicular direction, from the bottom of the flexible device, is less than about 2 cm, preferably about 1 cm.

Figure 9:
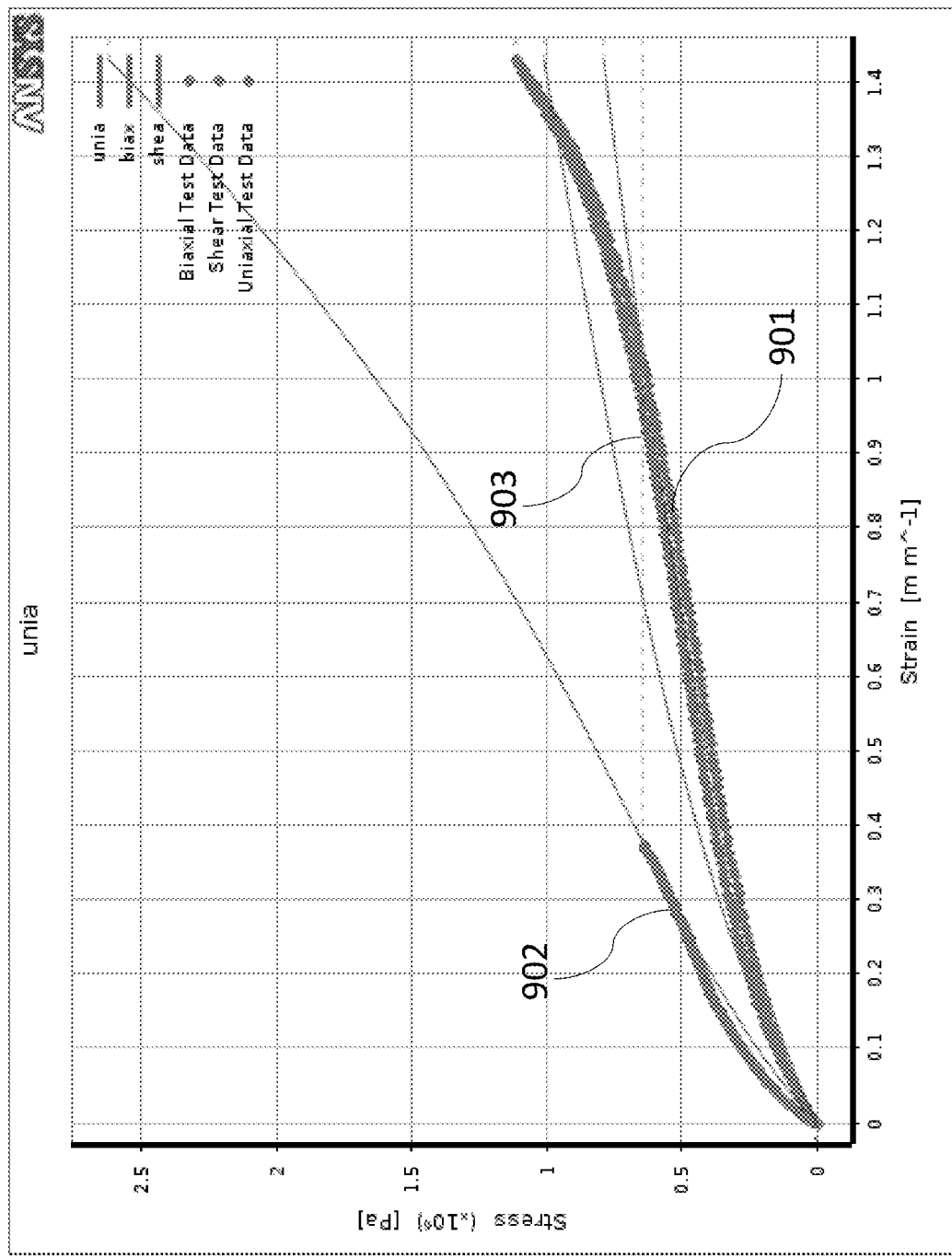
FIG. 9 shows results of a stress/strain simulation of the infusion set hub of FIG. 8.
Figure 10:
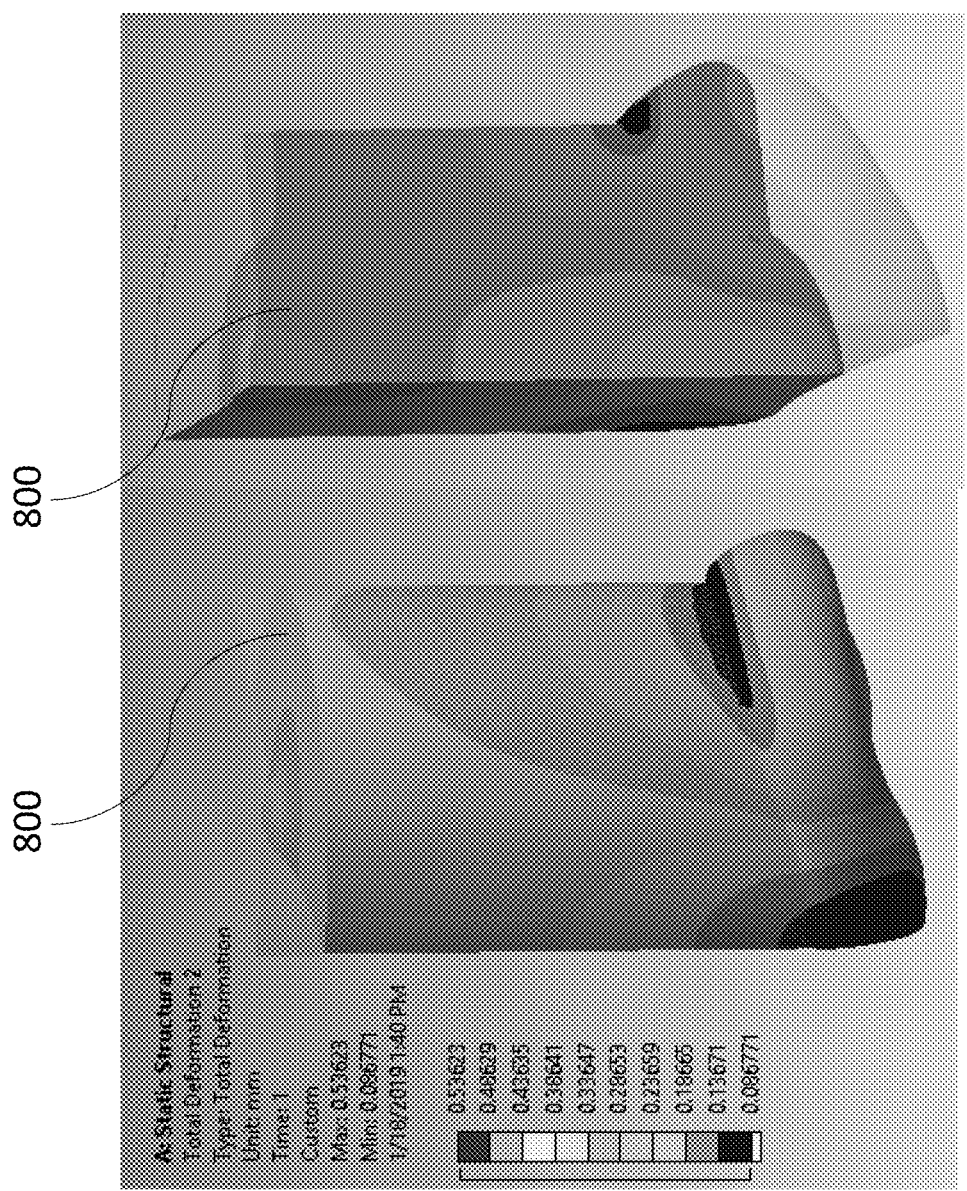
FIGS. 10 and 11 show further views an infusion set hub according to exemplary embodiments which was used in the stress/strain simulation.
Figure 11:
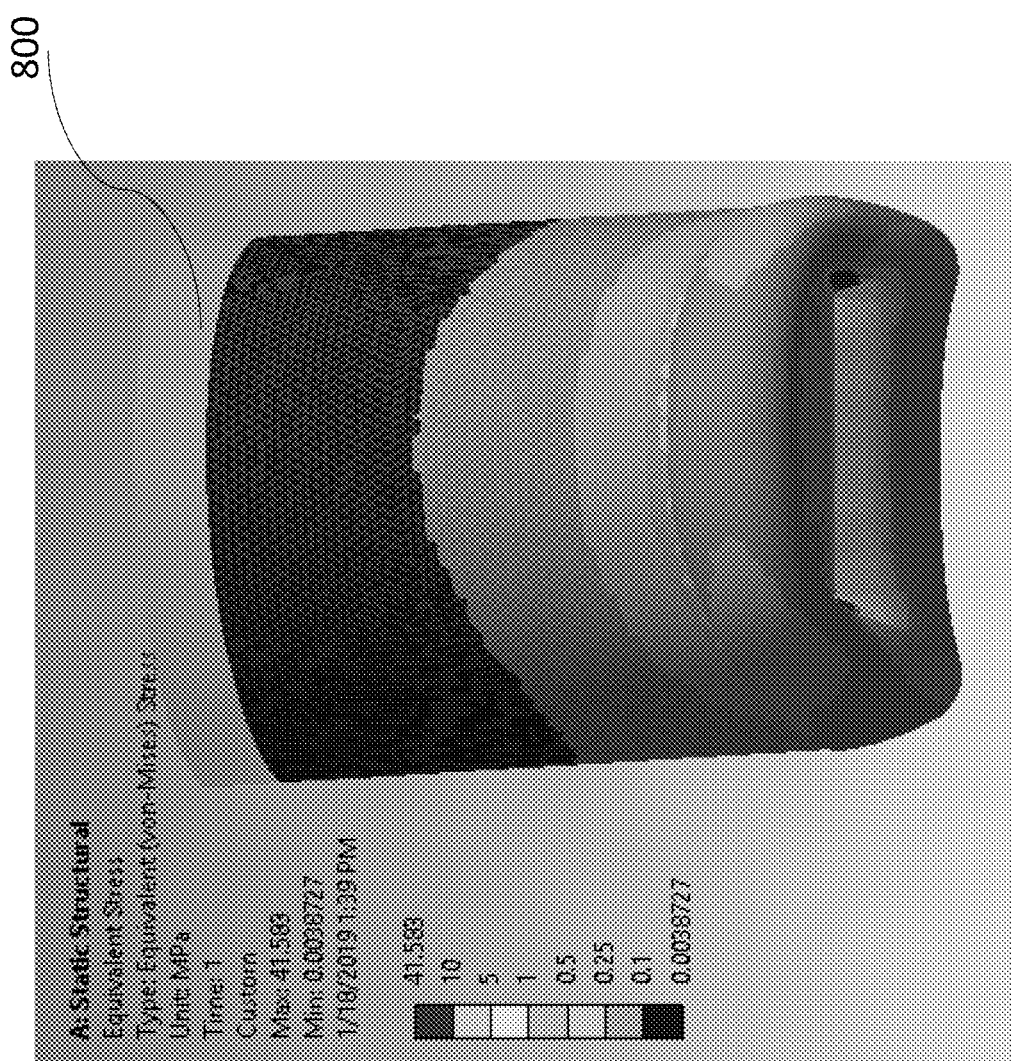

It is critical that the design of the combined device reduces the likelihood of a leak occurring during insulin delivery. FIGS. 8, 9, 10 and 11 show simulation designs and results for a combined device according to embodiments of the preset invention. In particular, the simulation results show that, with the combined device design disclosed herein, typical stress values caused by normal use of the combined device (such as stresses caused by everyday wear of the combined device and/or insertion of a cannula into the septum 800 of the infusion hub) will not be sufficient to cause a leak, even when the maximum vertical dimension of the combined device is constrained to about 1 cm. Previously, it was considered that infusion hubs with a constrained vertical dimension would be susceptible to developing leaks. However, as can be seen in FIG. 9, the infusion set hub of the combined device with this constrained vertical dimension was tested with varying amounts of uniaxial stress (line 901), biaxial stress (line 902) and shear stress (line 903). The resulting strains arising from each of these applied stresses was measured. On the basis of these stress/strain results, it was determined that typical stresses arising from everyday use of the combined device would not result in strains that could cause a leak. In the simulations, the infusion set hub material was chosen as polycarbonate, and the septum material inside the infusion set hub was chosen as rubber.

Figure 12:
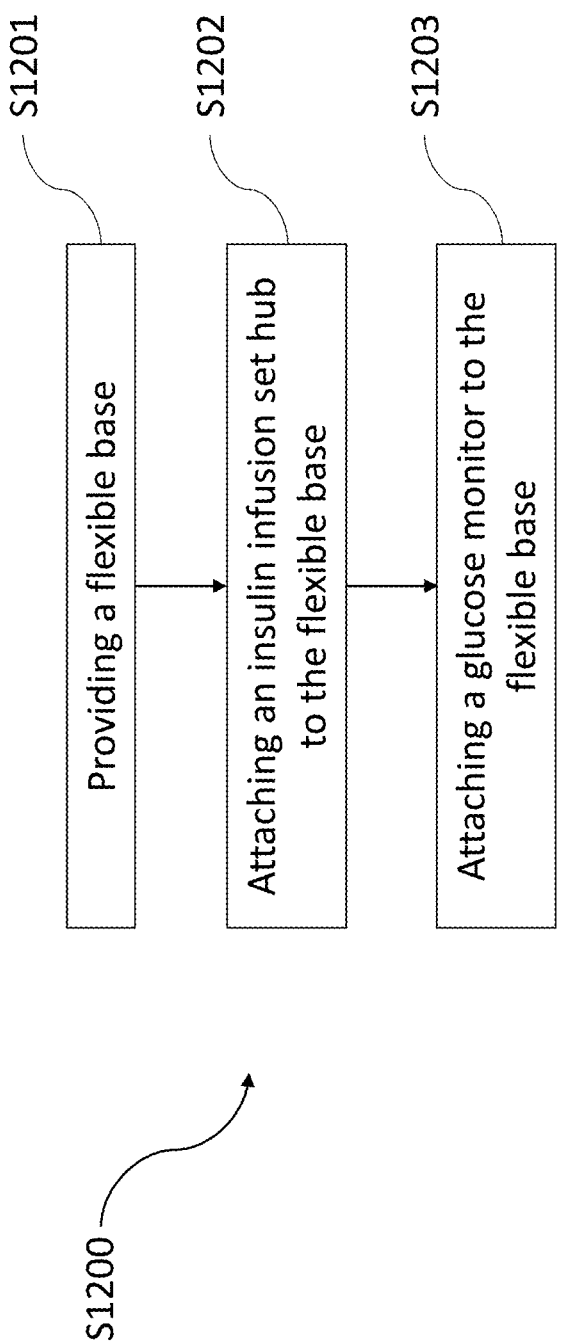
FIG. 12 shows a flowchart depicting a method of manufacturing a combined device in accordance with exemplary embodiments.

Turning to FIG. 12, a method S1200 of manufacturing a combined device in accordance with exemplary embodiments is shown in flowchart form. At step S1201, a flexible base is provided. The flexible base preferably has a Young's modulus sufficiently low that a movement of a first portion of the base causes substantially no movement in a second portion of the base remote from the first portion. After provision of the flexible base, the method progresses to step S1202.

At step S1202, an insulin infusion set hub is attached to the flexible base. In an exemplary embodiment, the insulin infusion set hub is welded to the flexible base, with a cannula of the insulin infusion set hub configured to protrude through the flexible base. After attachment of the insulin infusion set hub to the flexible base, the method progresses to step S803. In another exemplary embodiment, the insulin infusion set hub is attached to the flexible base using an adhesive.

At step S1203, a glucose sensor is attached to the flexible base. In an exemplary embodiment, the glucose sensor is welded to the flexible base, with a sensor probe of the glucose sensor configured to protrude through the flexible base. In another exemplary embodiment, the glucose sensor is attached to the flexible base using an adhesive.

For the sake of completeness, it will be appreciated that the order of performing steps S1202 and S1203 can be reversed if desired.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, embodiments of the insertion device may include computerized or mechanized components to adjust the force used in the installation of the infusion set hub, which components may employ various integrated circuit components, e.g., memory elements, digital signal processing elements, logic elements, look-up tables, or the like, which may carry out a variety of functions under the control of one or more microprocessors or other control devices.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to biosensor probe manufacturing may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

The invention claimed is:

1. A combined device comprising:
   an analyte sensor, the analyte sensor comprising a sensor probe;
   an infusion set hub, the infusion set hub comprising a cannula; and
   a flexible base, wherein the analyte sensor and the infusion set hub are indirectly attached to the flexible base, via a unitary piece of material that comprises a first connector, a second connector, and perforations formed between the first and second connectors, such that a movement of one of the analyte sensor and the infusion set hub does not cause a movement of the other one of the analyte sensor and the infusion set hub, wherein:
   the analyte sensor and the infusion set hub are permanently attached to a respective one of the first and second connectors;
   the first and second connectors are releasably attached to the flexible base to facilitate detaching of the first and second connectors from the flexible base; and
   the combined device is modular in that either one of the analyte sensor and the infusion set hub can be replaced without having to replace the combined device, by pulling apart the first and second connectors at the perforations.

2. The combined device of claim 1, wherein the analyte sensor comprises a transmitter configured to transmit sensed analyte concentration values to a user device.

3. The combined device of claim 1, wherein the analyte sensor and the infusion set hub are connected to each other via a joint.

4. The combined device of claim 3, wherein:
   the joint is configured to isolate movement of the analyte sensor from movement of the infusion set hub, and vice versa, while the analyte sensor and the infusion set hub are indirectly attached to the flexible base via the unitary piece of material, the joint comprising complementary angled sections of a housing of the analyte sensor and a housing of the infusion set hub; and
   either one of the analyte sensor and the infusion set hub can be individually replaced by decoupling the joint.

5. The combined device of claim 1, wherein the sensor probe and the cannula are spaced apart from one another by a distance of at least 5 mm.

6. The combined device of claim 1, wherein the sensor probe and the cannula are spaced apart from one another by a distance of at least 10 mm.

7. The combined device of claim 1, wherein the sensor probe and the cannula are spaced apart from one another by a distance of 13 mm.

8. The combined device of claim 1, wherein the infusion set hub is an insulin infusion set hub and comprises an insulin delivery tube and a connector configured to connect the insulin delivery tube to an insulin pump, and wherein the analyte sensor comprises a glucose sensor.

9. The combined device of claim 8, wherein the connector comprises a H-cap connector.

10. The combined device of claim 1, wherein a maximum vertical dimension of the combined device is 2 cm.

11. The combined device of claim 1, wherein each of the perforations extends all of the way through the unitary piece of material.

12. A combined device comprising:
   an analyte sensor comprising a sensor probe;
   an infusion set hub comprising a cannula; and
   a flexible base, wherein the analyte sensor and the infusion set hub are attached to the flexible base such that a movement of one of the analyte sensor and the infusion set hub while attached to the flexible base does not cause a movement of the other one of the analyte sensor and the infusion set hub while also attached to the flexible base;
   wherein the analyte sensor and the infusion set hub are releasably connected to each other via a joint configured to isolate movement of the analyte sensor from movement of the infusion set hub, and vice versa, the joint comprising complementary angled sections of a housing of the analyte sensor and a housing of the infusion set hub; and
   wherein the combined device is modular in that either one of the analyte sensor and the infusion set hub can be individually replaced without having to replace the combined device, by decoupling the joint.

13. The combined device of claim 12, wherein the analyte sensor and the infusion set hub are each releasably attached to the flexible base.

14. The combined device of claim 12, wherein the analyte sensor and infusion set hub are directly attached to the flexible base.

15. The combined device of claim 12, wherein the analyte sensor and infusion set hub are indirectly attached to the flexible base via first and second connectors, respectively.

16. The combined device of claim 12, wherein:
   the analyte sensor and the infusion set hub are indirectly attached to the flexible base, via a unitary piece of material that comprises a first connector, a second connector, and perforations formed between the first and second connectors;
   the analyte sensor and the infusion set hub are permanently attached to a respective one of the first and second connectors;
   the first and second connectors are releasably attached to the flexible base to facilitate detaching of the first and second connectors from the flexible base; and either one of the analyte sensor and the infusion set hub can be individually replaced by pulling apart the first and second connectors at the perforations.

17. A combined device comprising:

an analyte sensor comprising a sensor probe;

an infusion set hub comprising a cannula; and a flexible base, wherein the analyte sensor and the infusion set hub are attached to the flexible base such that a movement of one of the analyte sensor and the infusion set hub while attached to the flexible base does not cause a movement of the other one of the analyte sensor and the infusion set hub while also attached to the flexible base;

wherein the analyte sensor and the infusion set hub are releasably connected to each other via a joint configured to isolate movement of the analyte sensor from movement of the infusion set hub, and vice versa, the joint comprising a ball-and-socket joint; and wherein the combined device is modular in that either one of the analyte sensor and the infusion set hub can be individually replaced without having to replace the combined device, by decoupling the joint.

18. The combined device of claim 17, wherein the analyte sensor and the infusion set hub are each releasably attached to the flexible base.

19. The combined device of claim 17, wherein the analyte sensor and infusion set hub are directly attached to the flexible base.

20. The combined device of claim 17, wherein the analyte sensor and infusion set hub are indirectly attached to the flexible base via first and second connectors, respectively.

21. The combined device of claim 17, wherein:

the analyte sensor and the infusion set hub are indirectly attached to the flexible base, via a unitary piece of material that comprises a first connector, a second connector, and perforations formed between the first and second connectors;

the analyte sensor and the infusion set hub are permanently attached to a respective one of the first and second connectors;

the first and second connectors are releasably attached to the flexible base to facilitate detaching of the first and second connectors from the flexible base; and either one of the analyte sensor and the infusion set hub can be individually replaced by pulling apart the first and second connectors at the perforations.

* * * * *